(12) United States Patent
Liu et al.

(10) Patent No.: US 10,441,241 B2
(45) Date of Patent: Oct. 15, 2019

(54) REMOTE EXPOSURE CONTROL DEVICE, DIGITAL RADIOGRAPHY SYSTEM AND EXPOSING METHOD FOR THE SYSTEM

(71) Applicant: CareRay Digital Medical Technology Co., Ltd., Suzhou, Jiangsu Province (CN)

(72) Inventors: Jianqiang Liu, Suzhou (CN); Daming Ren, Suzhou (CN); Xianguo Huang, Suzhou (CN); Peng Gao, Suzhou (CN)

(73) Assignee: CareRay Digital Medical Technology Co., Ltd., Suzhou, Jiangsu Province (CN)

( * ) Notice: Subject to any disclaimer, the term of this patent is extended or adjusted under 35 U.S.C. 154(b) by 354 days.

(21) Appl. No.: 15/333,464

(22) Filed: Oct. 25, 2016

(65) Prior Publication Data

US 2017/0035383 A1   Feb. 9, 2017

Related U.S. Application Data

(63) Continuation of application No. PCT/CN2015/097421, filed on Dec. 15, 2015.

(30) Foreign Application Priority Data

Apr. 3, 2015  (CN) .......................... 2015 1 0158695
Sep. 22, 2015  (CN) .......................... 2015 1 0606717

(51) Int. Cl.
*A61B 6/00* (2006.01)
*A61B 5/1172* (2016.01)

(52) U.S. Cl.
CPC ............ *A61B 6/548* (2013.01); *A61B 6/4233* (2013.01); *A61B 6/4494* (2013.01); *A61B 6/467* (2013.01);

(Continued)

(58) Field of Classification Search
CPC ..... A61B 6/4233; A61B 6/4494; A61B 6/467; A61B 6/542; A61B 6/548; A61B 6/56
See application file for complete search history.

(56) References Cited

U.S. PATENT DOCUMENTS 6,094,589 A * 7/2000 Schmitt .................. A61B 6/467
378/210
6,801,594 B1 * 10/2004 Ali .......................... A61B 6/032
378/114

(Continued)

FOREIGN PATENT DOCUMENTS

CN       101152091 A      4/2008
CN       201725420 U      1/2011
(Continued)

OTHER PUBLICATIONS

International Search Report, dated Mar. 18, 2016, for International Application No. PCT/CN2015/097421, 3 pages.

*Primary Examiner* — Chih-Cheng Kao
(74) *Attorney, Agent, or Firm* — Seed IP Law Group LLP

(57) ABSTRACT

The present application relates to a remote exposure control device, a digital radiography system and an exposing method for the system. The remote exposure control device comprises: a power source module, a sensing module electrically connected to the power source module, a processing module electrically connected to the power source module, and a communication module, wherein: the sensing module is electrically connected to the communication module and the processing module respectively; the communication module is configured to communicate with a flat panel detector (FPD) paired with a digital radiography system; and the processing module is configured to, after receiving a trigger signal sent by the sensing module, control the communication module to send an awakening instruction or a power-on instruction to the FPD, so that the FPD is awak- (Continued)

ened from a sleeping state or a power-off state to a working state. Compared with the prior arts, the remote exposure control device of an embodiment can remotely control and monitor an FPD, facilitating realizing sciagraphing by one key and improving the work efficiency of users.

25 Claims, 5 Drawing Sheets

(52) U.S. Cl.
CPC ............ *A61B 5/1172* (2013.01); *A61B 6/542* (2013.01); *A61B 6/56* (2013.01); *A61B 2560/0242* (2013.01); *A61B 2560/0252* (2013.01); *A61B 2562/0204* (2013.01); *A61B 2562/029* (2013.01); *A61B 2562/0219* (2013.01)

(56) References Cited

U.S. PATENT DOCUMENTS

| | | | |
|---|---|---|---|
| 8,174,358 | B2 | 5/2012 | Butzine et al. |
| 8,364,241 | B2 | 1/2013 | Hannon et al. |
| 2003/0194056 | A1* | 10/2003 | Spahn ...................... A61B 6/08 378/205 |
| 2006/0239415 | A1* | 10/2006 | Liu ......................... A61B 6/583 378/207 |
| 2011/0050403 | A1* | 3/2011 | Liu ....................... A61B 6/4405 378/115 |
| 2011/0113329 | A1* | 5/2011 | Pusateri ................. G16H 40/63 715/702 |
| 2011/0291800 | A1* | 12/2011 | Butzine .................. A61B 6/544 378/108 |
| 2011/0306882 | A1 | 12/2011 | Hannon et al. |
| 2012/0201355 | A1 | 8/2012 | Butzine et al. |

FOREIGN PATENT DOCUMENTS

| | | |
|---|---|---|
| CN | 102258376 A | 11/2011 |
| CN | 102274035 A | 12/2011 |
| CN | 103202700 A | 7/2013 |
| CN | 204158403 U | 2/2015 |
| CN | 105142322 A | 12/2015 |
| JP | 5170432 B2 | 3/2013 |

\* cited by examiner

REMOTE EXPOSURE CONTROL DEVICE, DIGITAL RADIOGRAPHY SYSTEM AND EXPOSING METHOD FOR THE SYSTEM

BACKGROUND

Technical Field

The present application relates to the technical field of medical electronic devices, and more particularly to a remote exposure control device, a digital radiography system and an exposing method for the system.

Description of the Related Art

A remote exposure control device is a switch element for controlling an X-ray source in a digital radiography (DR) system and is frequently used.

An existing remote exposure control device only includes a mechanical two-stage pressing switch for controlling an X-ray source, which has monotonic functions and makes operations of a DR system complex.

BRIEF SUMMARY

An embodiment comprises a remote exposure control device, a digital radiography system and an exposing method for the system.

An embodiment of the present application provides a remote exposure control device for X-ray imaging. The remote exposure control device is configured to communicate with a pairing device in a digital radiography system and paired with the remote exposure control device so as to send communication data to the pairing device.

In an embodiment of the present application, the remote exposure control device comprises: a power source circuit or module, a processing circuit or module electrically connected to the power source module, and a communication circuit or module electrically connected to the power source module, wherein the processing module is configured to, after receiving a trigger signal, generate a control instruction and control the communication module to send the control instruction to the pairing device so as to change a working state of the pairing device.

In an embodiment of the present application, the remote exposure control device comprises: a sensing circuit or module electrically connected to the processing module and configured to send the trigger signal to the processing module.

In an embodiment of the present application, the control instruction is configured to awaken the pairing device from a sleeping state or a power-off state to an exposure stand-by state.

In an embodiment of the present application, the sensing module comprises a touch sensor configured to generate the trigger signal after sensing a touch operation.

In an embodiment of the present application, the touch sensor is a capacitive touch sensor configured to recognize a gesture instruction of a user and generate the trigger signal.

In an embodiment of the present application, the sensing module comprises an acceleration sensor configured to generate the trigger signal after sensing movement of the remote exposure control device.

In an embodiment of the present application, the sensing module comprises a camera configured to acquire identification information of one or more devices of the digital radiography system through scanning, such that the processing module pairs the remote exposure control device with the one or more devices of the digital radiography system.

In an embodiment of the present application, the sensing module comprises a temperature sensor and/or a humidity sensor.

In an embodiment of the present application, the remote exposure control device further comprises: an audio circuit or module electrically connected to the processing module and comprising at least one of an audio processing chip, a microphone and a speaker.

In an embodiment of the present application, the remote exposure control device comprises: an input circuit or module configured to input configuration information for the pairing device, wherein the processing module is configured to control the communication module to send the configuration information to the pairing device so as to configure parameters thereof.

In an embodiment of the present application, the remote exposure control device comprises: an output circuit or module configured to output state information of the pairing device received by the communication module.

In an embodiment of the present application, the pairing device is a flat panel detector (FPD).

An embodiment of the present application provides a remote exposure control device for X-ray imaging, the remote exposure control device being provided with a fingerprint recognition sensor.

An embodiment of the present application provides a remote exposure control device for X-ray imaging, the remote exposure control device being provided with an acceleration sensor.

An embodiment of the present application provides a digital radiography system, comprising: an X-ray source, a flat panel detector (FPD) and the remote exposure control device according to any of the above solutions.

An embodiment of the present application provides an exposing method for a digital radiography system, comprising: sending a control instruction to a pairing device that is already paired, after sensing a preset operation by a remote exposure control device; receiving by the pairing device the control instruction, and switching a working state of the pairing device to an exposure stand-by state; and controlling the digital radiography system by the remote exposure control device to complete exposing.

In an embodiment of the present application, the preset operation is a touch operation indicating a determined gesture instruction input in a designated area of the remote exposure control device.

In an embodiment of the present application, sensing the preset operation by the remote exposure control device comprises: receiving fingerprint information by a designated area of the remote exposure control device; and if the fingerprint information matches with stored fingerprint information, determining that the remote exposure control device senses the preset operation. The fingerprint information may be pre-stored, for example, in a memory.

In an embodiment of the present application, the preset operation is a change of a position of the remote exposure control device.

In an embodiment of the present application, the exposing method comprises: if the remote exposure control device does not sense the preset operation within a determined period, sending a sleeping or power-off instruction by the remote exposure control device to the pairing device; after receiving the sleeping or power-off instruction by the pairing device, switching the working state of the pairing device to a sleeping or power-off state. In an embodiment of the present application, before sending the control instruction to the pairing device that is already paired, the method comprises: pairing the remote exposure control device with the pairing device so that the remote exposure control device and the pairing device are capable of wirelessly communicating with each other.

In an embodiment of the present application, the method comprises: detecting an ambient temperature and/or an ambient humidity of the remote exposure control device; and if a detected ambient temperature and/or ambient humidity exceeds a preset safe range, sending by the remote exposure control device a visible alarm and/or an acoustic alarm.

In an embodiment of the present application, after switching the working state of the pairing device to the exposure stand-by state by the pairing device, the method comprises: receiving configuration information for the pairing device by the remote exposure control device, and sending the configuration information to the pairing device by the remote exposure control device; and receiving the configuration information by the pairing device, and configuring parameters of the pairing device by the pairing device.

In an embodiment of the present application, the method comprises: receiving state information of the pairing device by the remote exposure control device, and visibly outputting the state information.

DETAILED DESCRIPTION

Now, various embodiments will be described in detail with reference to the drawings. However, these embodiments are not intended to limit this disclosure, and modifications of the structures, methods or functions of these embodiments by those skilled in the art shall fall into the protection scope.

Figure 1:
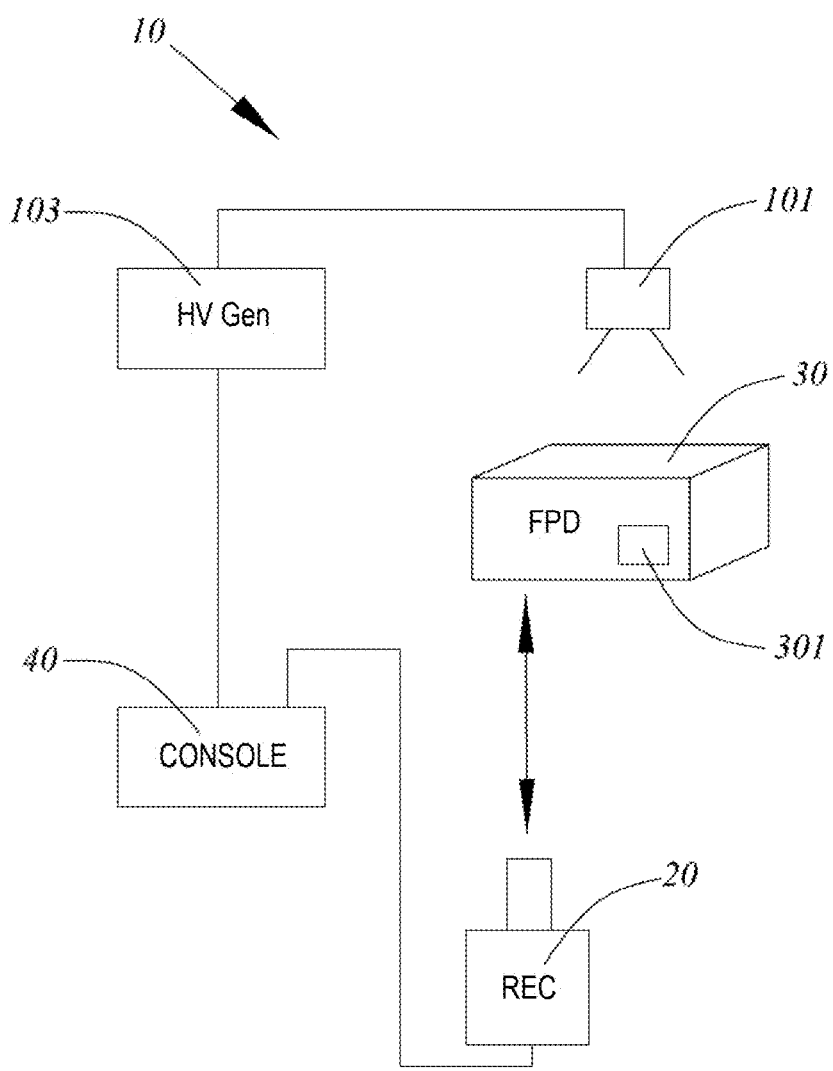
FIG. 1 is a schematic drawing of a digital radiography system according to an embodiment of the present application.
Figure 2:
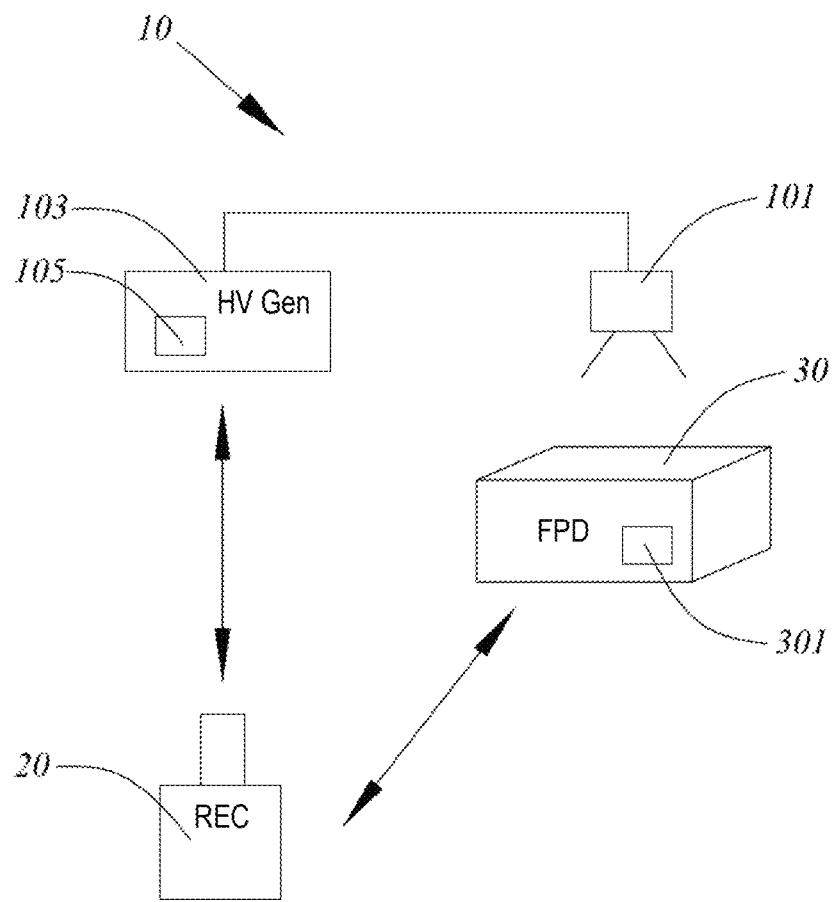
FIG. 2 is a schematic drawing of a digital radiography system according to another embodiment of the present application.

As shown in FIGS. 1-2, in a first embodiment, a digital radiography system comprises: an X-ray source 10, a remote exposure control device 20, a flat panel detector (FPD) 30 and a console 40.

One or more of the X-ray source 10, the FPD 30 and the console 40 may be paired with the remote exposure control device 20. After being paired with the remote exposure control device 20, the X-ray source 10, the FPD 30 and the console 40 may be called as pairing devices. The remote exposure control device 20 may communicate with the pairing devices and send communication data to the pairing devices. Of course, the remote exposure control device 20 may communicate with at least one of the pairing devices according to the needs.

In this way, the remote exposure control device 20 may interact with and remotely control the pairing devices, simplifying the operation procedures for the digital radiography system. For the ease of understanding, an example is described in which the FPD 30 is the pairing device. It should be understood that the X-ray source 10 and the console 40 may also interact with and control the remote exposure control device 20 as the FPD 30 does.

Further, the X-ray source 10 includes a tube assembly 101 and a high voltage generator 103, and may be connected to the console 40 by a cable. Generally, after the console 40 configures the parameters for the X-ray source 10 (for example, different human parts require different exposure parameters), exposure may be performed by a switch of the remote exposure control device 20. Of course, in this embodiment, the X-ray source 10 may be configured by the remote exposure control device 20 instead of the console 40, as shown in FIG. 2.

By exposure of the X-ray source 10, corresponding image information is acquired from and may be output from the FPD 30 in a visible manner for users.

Figure 3:
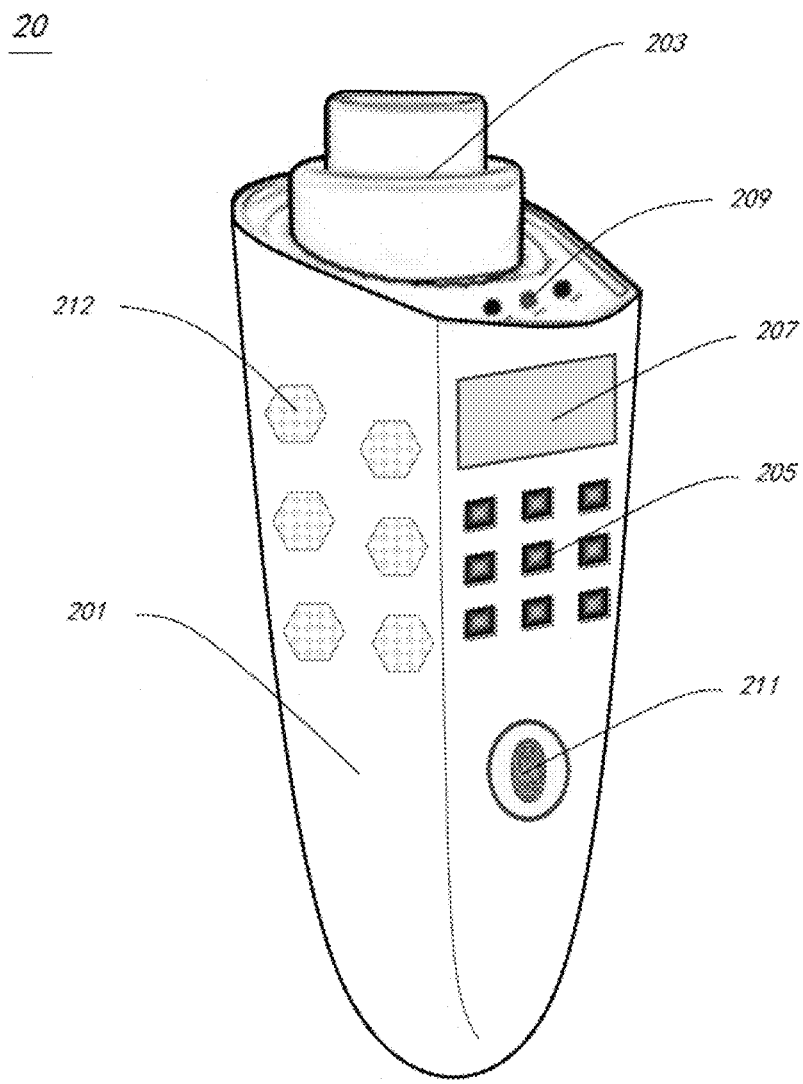
FIG. 3 is a perspective schematic drawing of a remote exposure control device according to an embodiment of the present application.

As shown in FIG. 3, the remote exposure control device 20 may be a hand switch, a foot switch or the like.

A hand switch is exemplified in this embodiment. Mechanically, the hand switch includes a body 201 for holding, a mechanical two-stage pressing switch 203 provided on the body 201, an input keyboard 205, a display screen 207, indication lamps 209, a fingerprint recognition area 211 and a touch sensing area 212. It can be understood that the two-stage pressing switch 203 may be provided as a non-mechanical one, the input keyboard 205 may not be physical keyboards (and may be provided as a touch screen for example), and the indication lamps 209, the fingerprint recognition area 211 and the touch sensing area 212 are optional. In this embodiment, FIG. 3 is illustrated for easy understanding of the technical solutions described herein.

Further, the body of the remote exposure control device 20 is provided with a control circuit 213 for the remote exposure control device.

Figure 4:
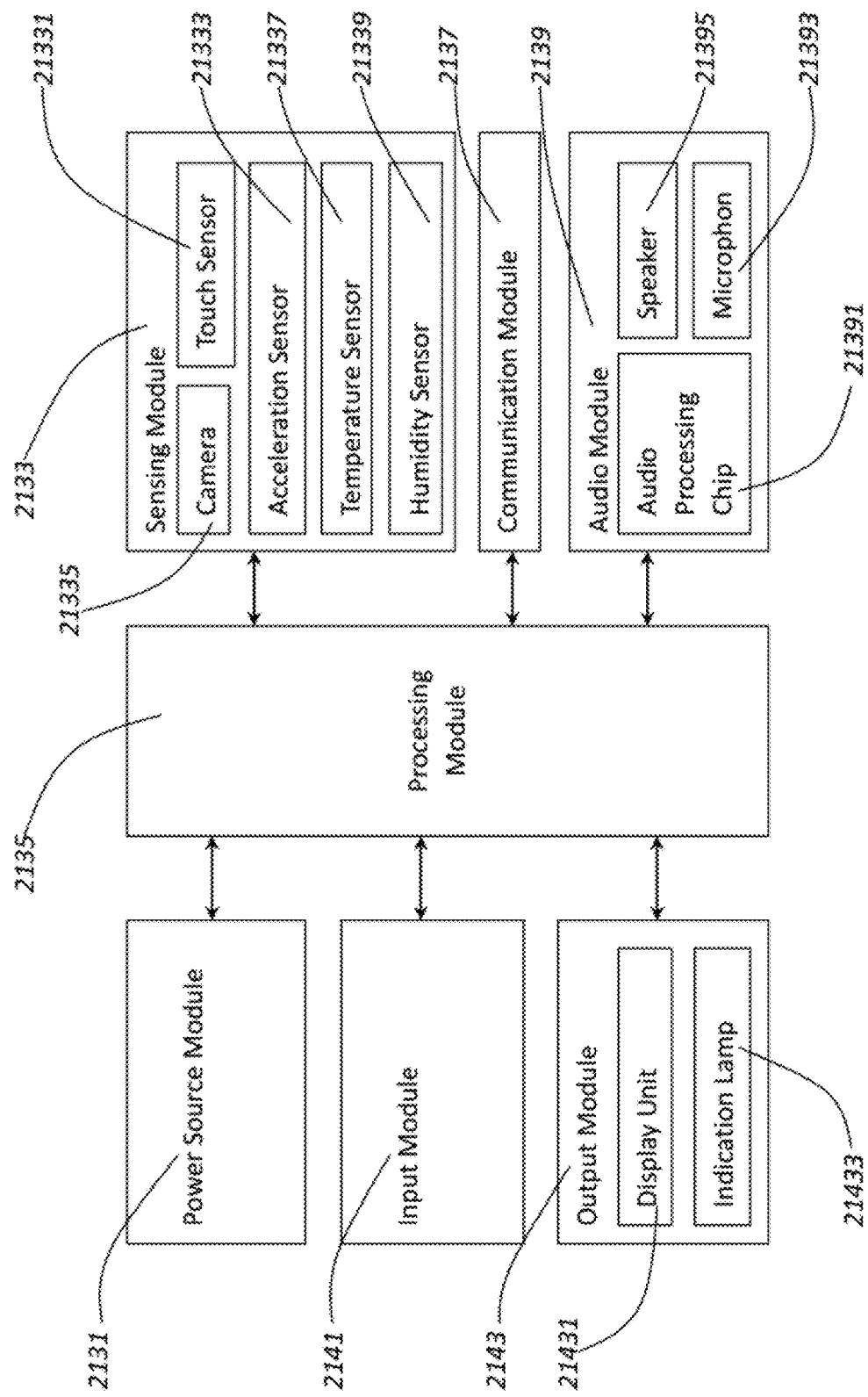
FIG. 4 shows the circuit modules of a remote exposure control device according to an embodiment of the present application.

As shown in FIG. 4 in this embodiment, the control circuit for the remote exposure control device includes a power source circuit or module 2131, a sensing circuit or module 2133 electrically connected to the power source module 2131, a processing circuit or module 2135 electrically connected to the power source module 2131, and a communication circuit or module 2137 (such as a Bluetooth module, a radio frequency module, a Wi-Fi module, an NFC module or the like). In fact, the power source module 2131 is electrically connected to all modules of the control circuit 213 so as to provide power thereto.

The sensing module 2133 and the communication module 2137 are electrically connected to the processing module 2135 respectively, and may communicate with one another.

The communication module 2137 is configured to communicate with the FPD 30, which is located in the digital radiography system and paired with the remote exposure control device.

In this embodiment, the processing module 2135 is configured to, after receiving a trigger signal, generate a control instruction and control the communication module 2137 to send the control instruction to the FPD 30 so as to change a working state of the FPD 30.

Specifically, the processing module 2135 is configured to, after receiving the trigger signal sent by the sensing module 2133, control the communication module 2137 to send the control instruction to the FPD 30, so that a communication module 301 provided on the FPD 30 receives the control instruction for changing a working state of the FPD 30. For example, the FPD 30 is awakened from a sleeping state or a power-off state to an exposure stand-by state (for example, the FPD 30 enters an AED mode).

Those skilled in the art can understand the power-off state, the sleeping state and the exposure stand-by state of the pairing device, which will not be described herein. In this embodiment, three examples are given below to explain how the sensing module 2133 generates the trigger signal.

1) The sensing module 2133 includes a touch sensor 21331, which may include a capacitive touch sensor and/or a fingerprint recognition sensor. When the touch sensor 21331 is a capacitive touch sensor, it is configured to recognize a gesture instruction of a user and generate the trigger signal. The touch sensor 21331 may cooperate with the touch sensing area 212 which is of a mechanical structure to sense gesture operations.

2) When the touch sensor 21331 is a fingerprint recognition sensor, it is configured to generate the trigger signal after a matching fingerprint is recognized, so that only specific persons can operate the digital radiography system. The fingerprint recognition sensor may cooperate with the fingerprint recognition area 211 which is of a mechanical structure to sense touch operations and collect fingerprints.

3) The sensing module 2133 includes an acceleration sensor 21333 configured to generate the trigger signal after sensing movement of the remote exposure control device. For example, when the remote exposure control device is picked up or swung, the acceleration sensor 21333 can generate the trigger signal, enhancing the convenience of using the remote exposure control device.

It should be noted that, in this embodiment, the touch sensor 21331 and the acceleration sensor 21333 may be provided in the sensing module 2133 separately or simultaneously. In this case, the sensing module 2133 may use the touch sensor 21331 or the acceleration sensor 21333 to generate the trigger signal. Of course, the trigger signal may be generated when the touch sensor 21331 receives a touch operation and the acceleration sensor 21333 senses movement of the remote exposure control device.

In this embodiment, the remote exposure control device 20 may be configured to switch the FPD 30 from the exposure stand-by state to the sleeping state or the power-off state. Specifically, the processing module 2135 is configured to, if the trigger signal is not received within a determined period, control the communication module 2137 to send a sleeping or power-off instruction to the FPD 30, so that the communication module 301 provided on the FPD 30 receives the sleeping or power-off instruction for switching the FPD 30 from the exposure stand-by state to the sleeping state or the power-off state.

Further, the sensing module 2133 may also include a camera 21335 configured to acquire identification information of one or more devices (the X-ray source 10, the FPD 30, the console 40, etc.) of the digital radiography system through scanning, such that the processing module 2135 pairs the remote exposure control device 20 with the one or more devices (the X-ray source 10, the FPD 30, the console 40, etc.) of the digital radiography system. The identification information of the one or more devices of the digital radiography system may be acquired by scanning a barcode/barcodes corresponding to the one or more devices of the digital radiography system.

In an embodiment, the camera 21335 may be also configured to collect human images, so that the processing module 2135 can perform identification verification to users through the human images. After the verification succeeds, the users may be allowed to use the remote exposure control device 20.

Further, the sensing module 2133 may also include a temperature sensor 21337 and/or a humidity sensor 21339. An example will be described below in which the sensing module 2133 includes a temperature sensor 21337 and a humidity sensor 21339. The temperature sensor 21337 may be configured to detect an ambient temperature of the remote exposure control device 20, and the humidity sensor 21339 an ambient humidity of the remote exposure control device 20. If a detected ambient temperature and/or ambient humidity of the remote exposure control device 20 exceeds a set safe range, the remote exposure control device 20 sends a visible alarm and/or an acoustic alarm, and stops exposing.

Those skilled in the art should understand that the touch sensor, the acceleration sensor, the camera, the temperature sensor and the humidity sensor may be integrally provided and communicate with the processing module 2135 via a bus; that these members may be provided separately and communicate with the processing module 2135 via multiple buses respectively; that these members may be integrated with other elements or circuits; and that for easy descriptions, these members are provided in the sensing module 2133 in this description.

Further, the control circuit for the remote exposure control device 20 includes an audio circuit or module 2139 electrically connected to the processing module 2135 and comprising at least one of an audio processing chip 21391, a microphone 21393 and a speaker 21395. The speaker 21395 may be configured to send alarms. In this embodiment, the audio module 2139 includes both the microphone 21393 and the speaker 21395. Thus, voice communication with patients can be realized through the audio module 2139 of the remote exposure control device 20.

Further, the control circuit for the remote exposure control device 20 includes an input circuit or module 2141 electrically connected to the processing module 2135 and configured to input configuration information for the FPD 30, wherein the processing module 2135 is configured to control the communication module 2137 to send the configuration information to the FPD 30, so that the communication module 301 of the FPD 30 receives the configuration information and configures the parameters for the FPD 30. The input module 2141 may cooperate with the input keyboard which is of a mechanical structure, so that the remote exposure control device 20 can receive configuration information input by users.

Further, the control circuit for the remote exposure control device 20 includes an output circuit or module 2143 configured to output state information (for example, information indicating a remaining power amount of the FPD 30 and information indicating whether the FPD 30 is ready) of the FPD 30 received by the communication module 2137 of the remote exposure control device. Of course, the output module 2143 may be also configured to output the configuration information when the configuration information is input. In an embodiment, the state information and the configuration information are output visibly. The output module 2143 includes a display unit 21431 which may cooperate with a display screen 207 which is of a mechanical structure, so that the remote exposure control device 20 can output the state information. In an example, the output module 2143 includes indication lamps 21433, which may act as another form of visible output for outputting the state information (for example, when the FPD is ready, an indication lamp is turned on). The indication lamps 21433 may also visibly output the alarms.

Figure 5:
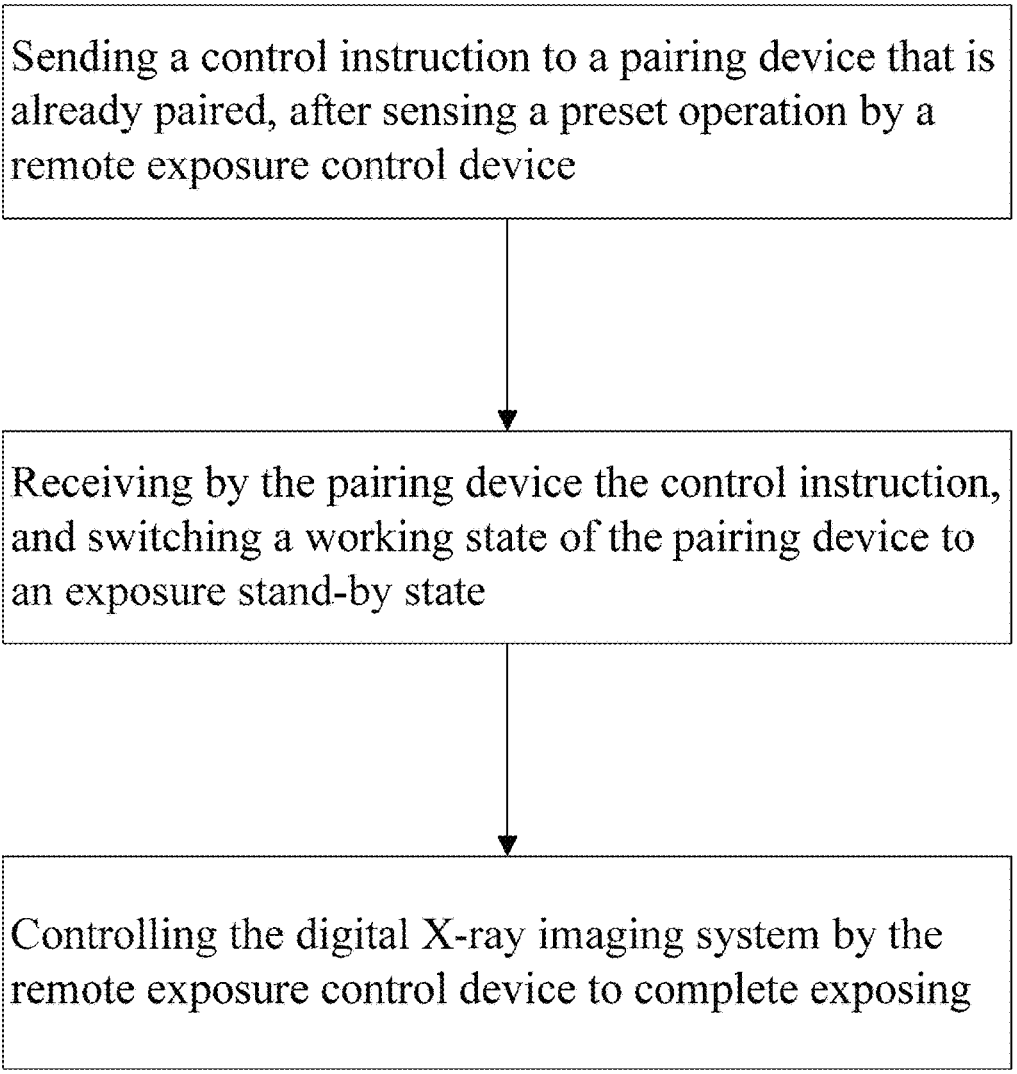
FIG. 5 is a flow chart of an exposing method for a digital radiography system according to an embodiment of the present application.

As shown in FIG. 5 in an embodiment, an exposing method for a digital radiography system comprises: sending a control instruction to a pairing device that is already paired, after sensing a determined or preset operation by a remote exposure control device; receiving by the pairing device the control instruction, and switching a working state of the pairing device to an exposure stand-by state (for example, the FPD 30 enters an AED mode); and controlling the digital radiography system by the remote exposure control device to complete exposing.

Exposing by the X-ray source under the control of the remote exposure control device may be performed through a two-stage switch of the remote exposure control device 20. Specifically, by pressing a first-stage switch, the high voltage generator of the X-ray source is pre-rotated. Then, a second-stage switch is pressed automatically or manually to complete exposing.

It can be understood that, in this embodiment, after the working state of the FPD is switched to the exposure-standby state, the first-stage switch is pressed; or the first-stage switch is pressed before the working state of the FPD is switched to the exposure-standby state; and alternatively, of course, the first-stage switch is pressed while the working state of the FPD is switched to the exposure-standby state.

Further, in this embodiment, three examples are given to describe the step of sending a control instruction to a pairing device that is already paired, after sensing a determined or preset operation by a remote exposure control device.

1) The preset operation is a touch operation indicating a determined gesture instruction input in a designated area of the remote exposure control device. That is, the sensing module 2133 senses a gesture operation by a finger on the touch sensing area 212. When a gesture operation on the touch sensing area 212 is sensed, the remote exposure control device 20 sends the control instruction to the paired FPD.

2) A designated area of the remote exposure control device receives fingerprint information. If the fingerprint information matches with stored fingerprint information, it is determined that the remote exposure control device senses the preset operation. That is, the sensing module 2133 senses a touch operation by a finger on the fingerprint recognition area 211 to collect fingerprints. When a matching fingerprint is recognized, the remote exposure control device 20 sends the control instruction to the paired FPD.

3) The preset operation is a change of a position of the remote exposure control device. That is, if the acceleration sensor 21333 senses a movement of the remote exposure control device (for example, when the remote exposure control device is picked up or swung), the remote exposure control device 20 sends the control instruction to the paired FPD.

It should be noted that the above methods may be used in succession in this embodiment to send an awaking or power-on instruction to the paired FPD. For example, if the fingerprint information matches with stored fingerprint information, and movement of the remote exposure control device 20 is sensed, the remote exposure control device 20 sends the control instruction to the paired FPD.

An embodiment of the exposing method for a digital radiography system comprises: if the remote exposure control device does not sense the set operation within a determined period, sending a sleeping or power-off instruction by the remote exposure control device to the paired FPD; after receiving the sleeping or power-off instruction by the paired FPD, switching the working state of the paired FPD to a sleeping or power-off state. The sleeping or power-off instruction is a type of a control instruction.

Switching the working state to the sleeping or power-off state may be performed by the sensing module, the processing module and the communication module.

Before sending the control instruction to the paired FPD, the method of an embodiment comprises: pairing the remote exposure control device with the FPD so that the remote exposure control device and the FPD is capable of wirelessly communicating with each other. In this embodiment, the camera 21335 may acquire the identification information of the FPD 30 by scanning, so that the processing module 2135 pairs the remote exposure control device 20 with the FPD 30. The identification information of the FPD 30 may be acquired by scanning a barcode/two-dimensional code corresponding to the FPD 30.

Before pairing the remote exposure control device with the FPD, the method may comprise: collecting human images using the camera 21335 so as to perform identification verification to users through the human images. After the verification succeeds, the users may be allowed to use the remote exposure control device 20.

In an embodiment, the method comprises: detecting an ambient temperature and/or an ambient humidity of the remote exposure control device; and if a detected ambient temperature and/or ambient humidity exceeds a preset safe range, sending by the remote exposure control device a visible alarm and/or an acoustic alarm, and stopping exposing.

The visible alarm may be output by the output module 2143, and the acoustic alarm by the audio module 2139.

After switching the working state of the FPD to the exposure stand-by state by the FPD, the method may comprise: receiving configuration information for the FPD by the remote exposure control device, and sending the configuration information to the FPD by the remote exposure control device; and receiving the configuration information by the FPD, and configuring parameters of the FPD by the FPD.

Inputting the configuration information into the remote exposure control device may be performed by the input module 2141.

The method may comprise: receiving state information (for example, information indicating a remaining power amount of the FPD and information indicating whether the FPD is ready) of the FPD by the remote exposure control device through radio frequency, and visibly outputting the state information. Outputting visible information may be performed by the output module 2143.

It should be noted that the exposing method of this embodiment is realized by the above X-ray imaging system. The hardware solutions corresponding to the exposing method, and the functional features of the respective modules of the hardware are described in FIGS. 2-3 and the corresponding descriptions, and will not be repeated herein.

As shown in FIG. 2 the second embodiment differs from the first one in that the remote exposure control device 20 can wirelessly communicate with both the FPD 30 and the X-ray source.

To sum up, the remote exposure control device of an embodiment simplifies the components of a digital radiography system and the connection among the components. In addition, the remote exposure control device of an embodiment can remotely interact with a pairing device paired therewith and remotely control the pairing device, facilitating realizing sciagraphing by one key and improving the work efficiency of users.

It should be noted that the above embodiments are only intended to illustrate rather than limit the technical solutions described herein. Although specific embodiments are described in detail through the above embodiments, those skilled in the art shall understand that modifications of the technical solutions or equivalent substitutions of some technical features of the above embodiments can be made without departing from the scope and spirit of the disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A remote exposure control device for X-ray imaging, comprising:
   processing circuitry;
   communication circuitry;
   at least one of a temperature sensor configured to detect an ambient temperature of the remote exposure control device and a humidity sensor configured to detect an ambient humidity of the remote exposure control device; and
   a sensing circuit, wherein, in operation,
   the remote exposure control device communicates with a pairing device in a digital radiography system and paired with the remote exposure control device so as to send control signals to the pairing device,
   the sensing circuit comprises a camera configured to collect human images and acquire identification information of one or more devices of the digital radiography system through scanning, and
   when the verification of human images and the verification of identification information passes sequentially, the pairing of the remote exposure control device with the one or more devices of the digital radiography system is successful.

2. The remote exposure control device of claim 1, comprising: a power source circuit, wherein the processing circuitry is electrically connected to the power source circuit, the communication circuitry is electrically connected to the power source circuit, and the processing circuitry is configured to, after receiving a trigger signal, generate a control instruction and control the communication circuitry to send the control instruction to the pairing device so as to change a working state of the pairing device.

3. The remote exposure control device of claim 2, wherein the sensing circuit is electrically connected to the processing circuitry and configured to send the trigger signal to the processing circuitry.

4. The remote exposure control device of claim 3, wherein the sensing circuit comprises an acceleration sensor configured to generate the trigger signal after sensing movement of the remote exposure control device.

5. The remote exposure control device of claim 2, wherein the control instruction is configured to awaken the pairing device from a sleeping state or a power-off state to an exposure stand-by state.

6. The remote exposure control device of claim 5, wherein the sensing circuit comprises a touch sensor configured to generate the trigger signal after sensing a touch operation.

7. The remote exposure control device of claim 6, wherein the touch sensor is a capacitive touch sensor configured to recognize a gesture instruction of a user and generate the trigger signal.

8. The remote exposure control device of claim 1, wherein the remote exposure control device is configured as a hand switch, wherein the hand switch comprises a body for holding, a two-stage pressing switch provided on the body, an input keyboard, a display screen, indication lamps, a fingerprint recognition area and a touch sensing area all provided on the body.

9. The remote exposure control device of claim 1, comprising: an audio circuit electrically connected to the processing circuitry and comprising at least one of an audio processing chip, a microphone and a speaker.

10. The remote exposure control device of claim 1, comprising: an input circuit configured to input configuration information for the pairing device, wherein the processing circuitry is configured to control the communication circuitry to send the configuration information to the pairing device so as to configure parameters thereof.

11. The remote exposure control device of claim 1, comprising: an output circuit configured to output state information of the pairing device received by the communication circuitry.

12. The remote exposure control device of claim 1, wherein the pairing device is a flat panel detector (FPD).

13. A digital radiography system, comprising: an X-ray source, a flat panel detector (FPD) and the remote exposure control device according to claim 1.

14. A remote exposure control device for X-ray imaging, the remote exposure control device comprising:
   control circuitry;
   a switch;
   a sensing circuit; and
   a touch sensor, wherein in operation,
   the touch sensor recognizes a gesture instruction of a user and the control circuitry generates control signals based on recognized gesture instructions,
   exposure is controlled by the switch,
   the sensing circuit comprises a camera configured to collect human images and acquire identification information of one or more devices of a digital radiography system through scanning,
   when the verification of human images and the verification of identification information passes sequentially, pairing of the remote exposure control device with the one or more devices of the digital radiography system is successful, and
   when the touch sensor recognizes a gesture instruction of a user, the remote exposure control device sends a control instruction to a pairing device in the digital radiography system and paired with the remote exposure control device so as to awaken the pairing device from a sleeping state or a power-off state to an exposure stand-by state.

15. A remote exposure control device for X-ray imaging, the remote exposure control device comprising:
   control circuitry;
   an acceleration sensor;
   a switch; and
   a sensing circuit, wherein in operation,
   the control circuitry generates control signals based on acceleration data generated by the acceleration sensor, exposure is controlled by the switch, the sensing circuit comprises a camera configured to collect human images and acquire identification information of one or more devices of a digital radiography system through scanning, when the verification of human images and the verification of identification information passes sequentially, the pairing of the remote exposure control device with the one or more devices of the digital radiography system is successful, and when the acceleration sensor senses movement of the remote exposure control device, the remote exposure control device sends a control instruction to a pairing device in the digital radiography system and paired with the remote exposure control device so as to awaken the pairing device from a sleeping state or a power-off state to an exposure stand-by state.

16. A remote exposure control device for X-ray imaging, the remote exposure control device comprising:

control circuitry;

a switch;

a sensing circuit; and a fingerprint recognition sensor, wherein in operation, the control circuitry generates control signals based on fingerprint recognition data generated by the fingerprint recognition sensor;

exposure is controlled by the switch, the sensing circuit comprises a camera configured to collect human images and acquire identification information of one or more devices of a digital radiography system through scanning, when the verification of human images and the verification of identification information passes sequentially, the pairing of the remote exposure control device with the one or more devices of the digital radiography system is successful, when the fingerprint recognition sensor recognizes a matching fingerprint, the remote exposure control device sends a control instruction to a pairing device in the digital radiography system and paired with the remote exposure control device so as to awaken the pairing device from a sleeping state or a power-off state to an exposure stand-by state.

17. An exposing method for a digital radiography system, comprising:

collecting human images and acquiring identification information of one or more devices of the digital radiography system through scanning, when verification of human images and verification of identification information passes sequentially, pairing of a remote exposure control device with the one or more devices of the digital radiography system is successful;

sending a control instruction to a pairing device that is already paired, after sensing a determined operation by the remote exposure control device;

receiving by the pairing device the control instruction, and switching a working state of the pairing device to an exposure stand-by state;

controlling the digital radiography system by the remote exposure control device to complete exposing;

detecting an ambient temperature and/or an ambient humidity of the remote exposure control device; and when a detected ambient temperature and/or ambient humidity exceeds a determined safe range, activating, by the remote exposure control device, a visible alarm and/or an acoustic alarm.

18. The exposing method of claim 17, wherein the determined operation is a touch operation indicating a determined gesture instruction input in a designated area of the remote exposure control device.

19. The exposing method of claim 17, wherein sensing the determined operation by the remote exposure control device comprises:

receiving fingerprint information by a designated area of the remote exposure control device; and when the fingerprint information matches with stored fingerprint information, determining that the remote exposure control device senses the determined operation.

20. The exposing method of claim 17, wherein the determined operation is a change of a position of the remote exposure control device.

21. The exposing method of claim 17, comprising:

when the remote exposure control device does not sense the determined operation within a determined period, sending a sleeping or power-off instruction by the remote exposure control device to the pairing device;

after receiving the sleeping or power-off instruction by the pairing device, switching the working state of the pairing device to a sleeping or power-off state.

22. The exposing method of claim 17, wherein before sending the control instruction to the pairing device that is already paired, the method comprises: pairing the remote exposure control device with the pairing device so that the remote exposure control device and the pairing device are capable of wirelessly communicating with each other.

23. The exposing method of claim 17, wherein before or after or at the same time of switching a working state of the pairing device to an exposure stand-by state, actuating a first-stage switch; and then actuating a second-stage switch to complete exposing.

24. The exposing method of claim 17, wherein after switching the working state of the pairing device to the exposure stand-by state by the pairing device, the method comprises:

receiving configuration information for the pairing device by the remote exposure control device, and sending the configuration information to the pairing device by the remote exposure control device; and receiving the configuration information by the pairing device, and configuring parameters of the pairing device by the pairing device.

25. The exposing method of claim 17, comprising:

receiving state information of the pairing device by the remote exposure control device, and visibly outputting the state information.

* * * * *